(12) United States Patent
Scheker

(10) Patent No.: US 8,052,757 B1
(45) Date of Patent: Nov. 8, 2011

(54) COMBINED TOTAL WRIST AND TOTAL DISTAL RADIOULNAR JOINT PROSTHESIS

(75) Inventor: Luis Roman Scheker, Glenview, KY (US)

(73) Assignee: Aptis Medical, LLC, Louisville, KY (US)

( * ) Notice: Subject to any disclaimer, the term of this patent is extended or adjusted under 35 U.S.C. 154(b) by 1596 days.

(21) Appl. No.: 11/306,311

(22) Filed: Dec. 22, 2005

Related U.S. Application Data

(60) Provisional application No. 60/726,113, filed on Oct. 13, 2005.

(51) Int. Cl.
*A61F 2/42* (2006.01)
(52) U.S. Cl. .................................................. 623/21.13
(58) Field of Classification Search .... 623/20.11–20.13, 623/21.11–21.17
See application file for complete search history.

(56) References Cited

U.S. PATENT DOCUMENTS

| | | | |
|---|---|---|---|
| 3,875,594 A | 4/1975 | Swanson | |
| 4,106,128 A | 8/1978 | Greenwald et al. | |
| 4,158,893 A | 6/1979 | Swanson | |
| 4,164,793 A | 8/1979 | Swanson | |
| 4,178,640 A | 12/1979 | Buechler et al. | |
| 4,180,871 A | 1/1980 | Hamas | |
| 4,198,713 A | 4/1980 | Swanson | |
| 4,229,841 A | 10/1980 | Youm | |
| 4,349,922 A | 9/1982 | Agee | |
| 4,784,661 A | 11/1988 | Beckenbaugh et al. | |
| 5,108,444 A | 4/1992 | Branemark | |
| 5,133,762 A | 7/1992 | Branemark | |
| 5,314,485 A | 5/1994 | Judet | |
| 5,326,364 A | 7/1994 | Clift, Jr. et al. | |
| 5,458,646 A | 10/1995 | Giachino et al. | |
| 5,507,821 A | 4/1996 | Sennwald et al. | |
| 5,702,470 A | 12/1997 | Menon | |
| 5,782,926 A | 7/1998 | Lamprecht | |
| 5,951,604 A | 9/1999 | Scheker | |
| 6,059,832 A | 5/2000 | Menon | |
| 6,168,630 B1 | 1/2001 | Keller et al. | |
| 6,221,073 B1 | 4/2001 | Weiss et al. | |
| 6,284,000 B1 * | 9/2001 | Ege | 623/21.11 |
| 6,485,520 B1 * | 11/2002 | Hubach et al. | 623/21.13 |
| 6,712,820 B2 | 3/2004 | Orbay | |
| 2002/0010511 A1 * | 1/2002 | Michelson | 623/17.15 |
| 2006/0004462 A1 | 1/2006 | Gupta | |

FOREIGN PATENT DOCUMENTS

DE 10043107 C1 9/2002

(Continued)

OTHER PUBLICATIONS

Acumed, Acu-Loc Targeted Distal Radius System.

(Continued)

*Primary Examiner* — David Isabella
*Assistant Examiner* — Ann Schillinger
(74) *Attorney, Agent, or Firm* — Camoriano and Associates; Theresa Fritz Camoriano; Guillermo Camoriano

(57) ABSTRACT

A total wrist and distal radioulnar joint replacement prosthesis includes a radial brace member to be secured to the radius bone, an ulna brace member to be secured to the ulna bone, and an articular member to be secured to the carpal bones. The articular member is slidably received in a socket in the radial brace member and is supported by the ulna bone.

15 Claims, 5 Drawing Sheets

FOREIGN PATENT DOCUMENTS

| | | |
|---|---|---|
| DE | 10237016 | 2/2004 |
| EP | 34 192 | 8/1981 |
| FR | 2660856 | 10/1991 |
| GB | 2269752 | 8/1993 |
| WO | 92/00709 | 1/1992 |
| WO | WO 01/01892 A1 | 1/2001 |

OTHER PUBLICATIONS

Hand Innovations, The Anatomical DVR Surgical Technique, from web site.
Kinetikos Medical Incorporated, Universal 2 Total Wrist Implant System, from web site.
Small Bone Innovations, uHead Ulnar Implant System, from web site.
Small Bone Innovations, Total Wrist Implant, from web site.
Stryker, Universal Distal Radius System, from web site.
Wright, Evolve Radial Head Plate, from web site.
Wright, Locon VLS Distal Radius System, from web site.
CFV Wrist System, Biomet, Inc., Form No. Y-BMT-152/013190.
'Clinical Mechanics of the Hand', Second Edition, 1993 by Mosby—Year Book, Inc., St. Louis, MO.
Silastic HP 100 Swanson Finger Joint Implant and Dow Corning Wright Swanson Finger Joint Grommet II, Dow Corning Wright Catalog.
Sutter Implants for the Hand and Forearm, brochure by Sutter Corporation; 4 pages; dated Feb. 12, 1990.
The Journal of Bone and Joint Surgery, vol. 69-A, No. 7, Sep. 1987, Jayasanker Menon, MD, 'Total Wrist Replacement Using the Modified Volz Prosthesis'.
The Journal of Hand Surgery, vol. 20A No. 1, Hans Christoph Meuli, MD, et al.,. Jan. 1995, "Uncemented Total Wrist Arthroplasty", pp. 115-121, 802.
Mayo Clinic College of Medicine, 200 First Street SW, Rochester, MN 55905; 'Use of an Ulnar Head Endoprosthesis for treatment of an unstable distal ulnar resection: Review of mechanics, indications, and surgical technique.' 2005 Elsevier Inc.

\* cited by examiner

COMBINED TOTAL WRIST AND TOTAL DISTAL RADIOULNAR JOINT PROSTHESIS

This application claims priority from U.S. Provisional Application Ser. No. 60/726,113 filed Oct. 13, 2005, which is hereby incorporated by reference.

BACKGROUND

The present invention relates to a wrist and distal radioulnar joint prosthesis. One problem with current wrist replacement technologies is that they do not provide sufficient support to enable the patient to lift objects of any substantial weight.

SUMMARY

The present invention provides a wrist and distal radioulnar joint prosthesis that gives the patient a wide range of motion, the ability to grip, and the ability to lift objects with the affected hand.

DESCRIPTION

Figure 1:
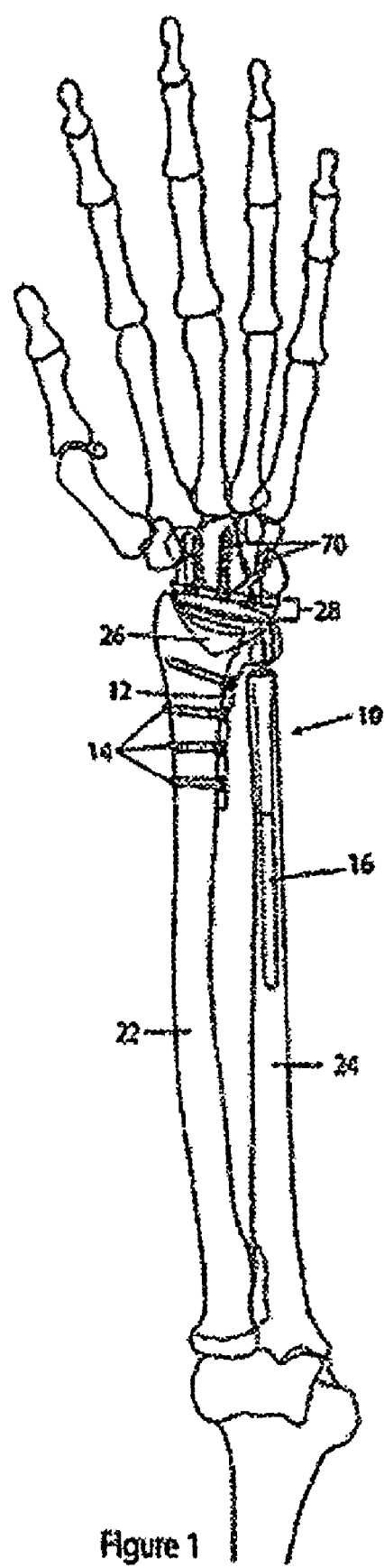
FIG. 1 is a front view of a wrist and distal radioulnar joint prosthesis made in accordance with the present invention installed on a human skeleton.
Figure 2:
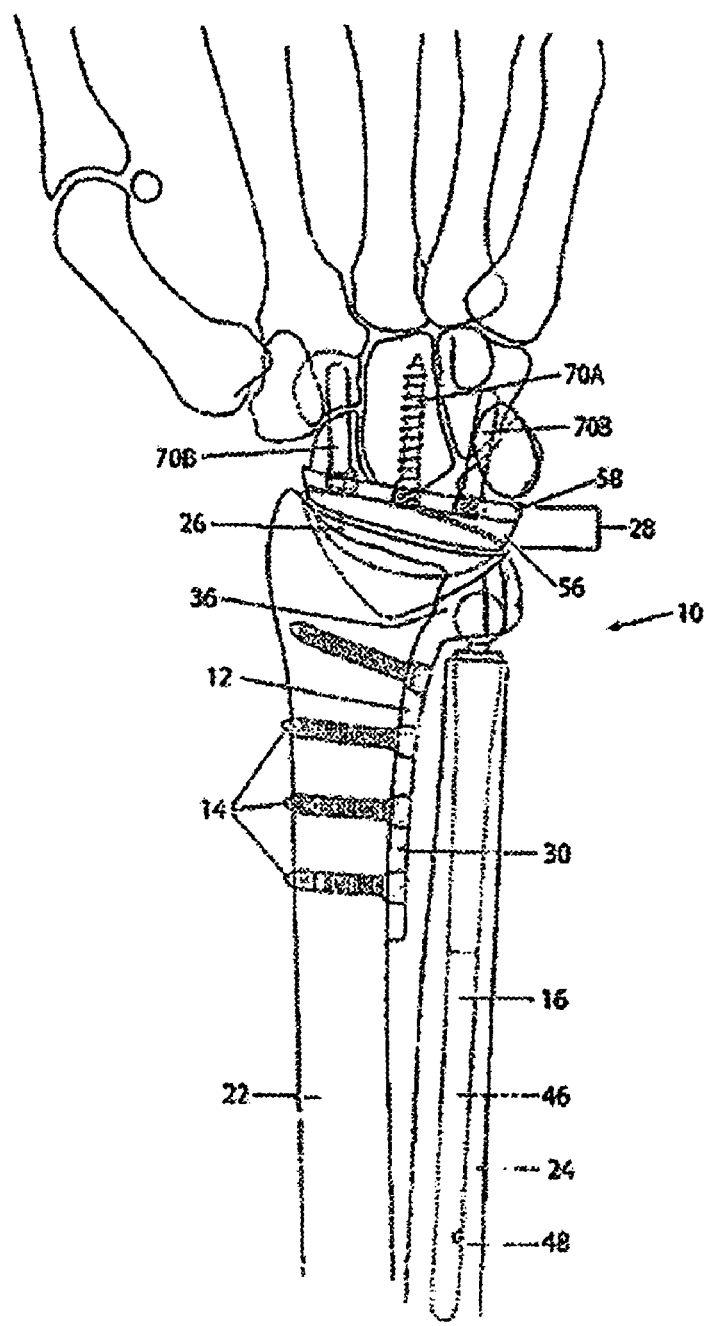
FIG. 2 is an enlarged view of the installed wrist and distal radioulnar joint prosthesis of FIG. 1.
Figure 3:
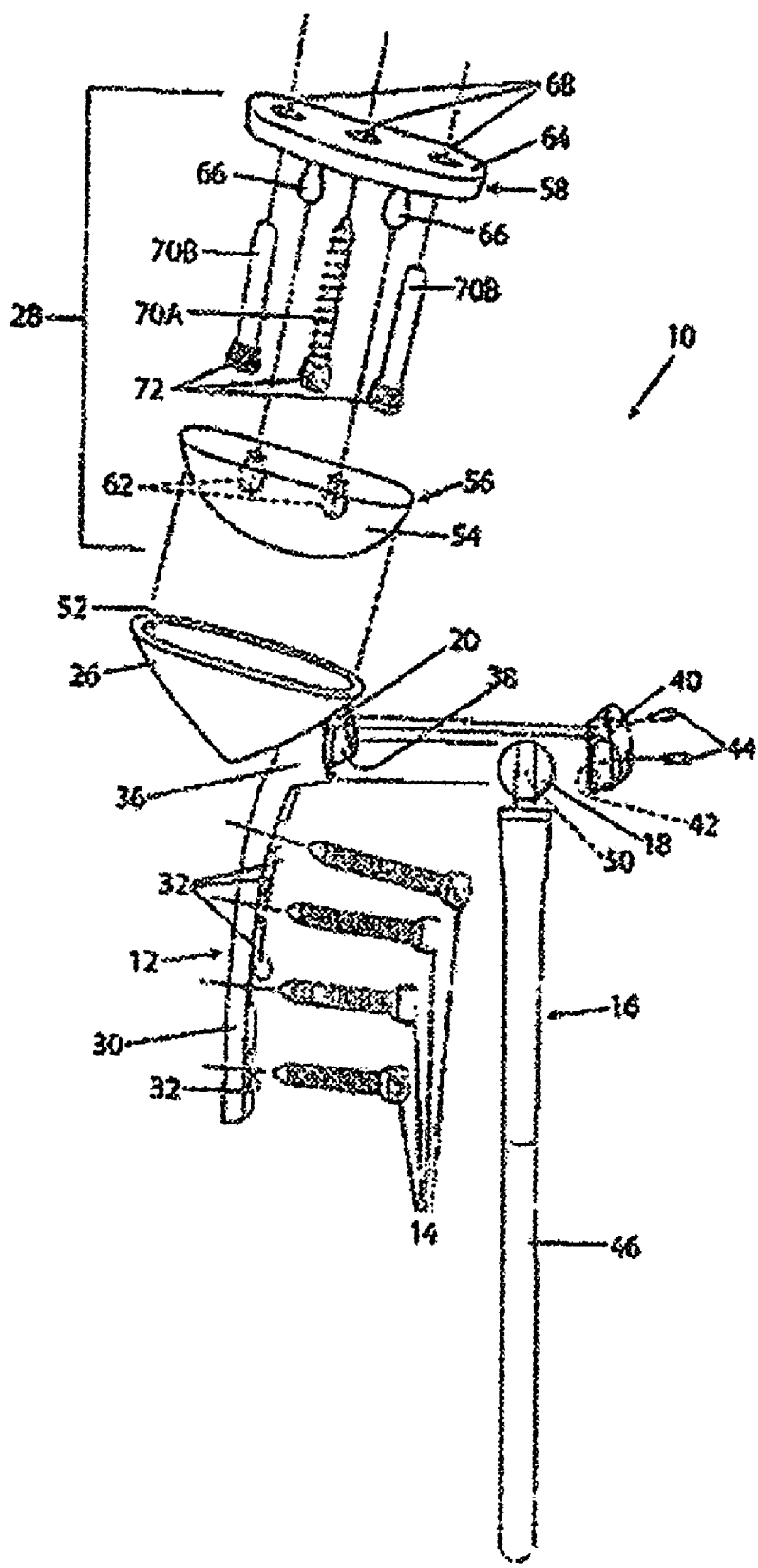
FIG. 3 is an exploded perspective view of the wrist and distal radioulnar joint prosthesis of FIG. 2.

FIGS. 1-3 show one embodiment of a wrist and distal radioulnar joint prosthesis 10 made in accordance with the present invention. The wrist and distal radioulnar joint prosthesis 10 includes a radial brace member 12, which is secured to the radius bone 22 with a plurality of screws 14. This brace member 10 replaces the radial half of the radiocarpal joint and replaces the sigmoid notch of the radius. Also included is an ulnar brace member 16, which is secured to the ulna bone 24, typically via a press fit into the medullary cavity 48 of the ulna 24. In addition to (or instead of) the press fit, the brace member 16 may be cemented, adhered, or secured by other means to the ulna 24. The ulnar brace member 16 is essentially a shaft, symmetrical about a central axis. A spherical ball 18 is mounted onto the brace member 16 at one end. The ball 18 has bore 50 along its diameter which receives the reduced cross-section end of the brace member 16. The ball 18 is free to pivot about the axis of the brace member 16. A spherical recess is formed by the base 20 at the distal end of the radial brace 12 and by the cover 40, which is secured to the base 20 by means of screws 44. The spherical recess defines a center point. The spherical ball 18 is received in that slightly larger spherical recess and is free to swivel within that spherical recess, in order to support the radius 22 relative to the ulna 24 for pronation and supination of the wrist. The ulnar brace member 16 combined with the spherical ball 18 replaces the ulna head.

Referring to FIGS. 2 and 3, the radial brace member 12 includes an elongated portion 30, which has a radius abutment surface that lies adjacent to the outer surface of the radius bone 22 and conforms to the shape of the radius bone 22, and which is secured to the radius 22 by means of screws 14 that extend through openings 32 in the elongated portion 30. The distal end 36 of the radial brace member 12 terminates in a base 20 which defines a hemispherical portion 38 of the spherical cavity. The base cover 40 defines another hemispherical portion 42 of the spherical cavity. When the ball 18 is trapped between the base cover 40 and the base 20, it is supported in the spherical cavity formed by the hemispherical portions 38, 42. The base cover 40 replaces the ligamentus structures of the Distal Radioulnar Joint.

The ulnar brace member 16 includes an elongated ulnar stem rod 46 which is inserted into a medullary cavity 48 (See FIG. 2) of the ulna 24. The ulnar stem rod 46 may be press fit or may be cemented into this medullary cavity 48. The distal end of the ulnar stem rod 46 is received in a bore 50 through the diameter of the ball 18 so as to permit translational movement of the ulnar stem rod 46 relative to the ball 18 along the axis of the ulnar brace member 16.

As indicated above, the ball 18 also is able to pivotably rotate within the spherical cavity formed by the base 20 and the base cover 40. This combination provides support of the radius 22 relative to the ulna 24 through the full range of motion from pronation to supination of the hand and forearm. The portion of the prosthesis 10 described thus far is essentially identical to a distal radioulnar joint replacement prosthesis described in U.S. Pat. No. 5,951,604 "Scheker", which is hereby incorporated herein by reference.

The wrist and distal radioulnar joint prosthesis 10 further includes an articular socket 26, which is fixed relative to the radial brace member 12 by being an integral part of the radial brace member 12. It is understood that the articular socket 26 could be a separate piece which is fixed to the radial brace member 12 by such means as welding, bolting, snapping together, or any other suitable means. An articular member 28 fits into and slides relative to the articular socket 26.

The articular socket 26 defines a concave ellipsoidal surface 52 (which may also be referred to as a reverse-ellipsoidal surface) which receives the mating convex ellipsoidal surface 54 of the articular member 28 as described in more detail below. Since the articular socket 26 is fixed to the radial brace member 12, it is supported by and secured to the radius 22 as well as being supported by the ulna 24 through the ball joint. When mounting the radial brace member 12 onto the radius bone 22, it may be necessary to excise some of the distal end of the radius to accommodate the articular socket 26.

In this embodiment, the articular member 28 includes a base 56 and a distal plate 58. The base 56 defines the convex ellipsoidal surface 54 which mates with and slidably engages the concave ellipsoidal surface 52 of the articular socket 26 for rotation of the base 56 relative to the articular socket 26. The base 56 further has a substantially flat top surface 60, which defines two tear-shaped cavities 62 for the attachment of the distal plate 58 to the base 54, as described below.

The distal plate 58 is a substantially flat member 64 which has two downwardly-extending tear-shaped projections 66. These projections 66 are sized to snap-fit into the corresponding tear-shaped cavities 62 in the base 56 in order to secure the distal plate 58 to the base 56. The distal plate 58 further defines three through openings 68 to accommodate elongated fasteners 70A, 70B, which secure the distal plate 58 to the carpal bones of the hand. The fasteners in this embodiment are a screw 70A and two pegs 70B, as shown in FIG. 3. Each of these fasteners 70A, 70B includes a threaded portion 72 at the head end, which includes self-locking threads that are threaded and locked into a corresponding threaded surface in the respective opening 68 of the distal plate 58.

In this particular embodiment, the metal components of the prosthesis 10 are made from cobalt chromium. These metal components include the brace members 12 and 16, the securing screws 14, 44, 70A, and pegs 70B, the articular socket 26, and the distal plate 58 and its two tear-shaped projections 66. The non-metal components are made from an ultra-high molecular weight polymer, such as UHMW polyethylene. These non-metal components include the ball 18 and the base 56 of the articular member 28.

To assemble and install the wrist and distal radioulnar joint prosthesis 10, first the distal radioulnar joint is installed as described in the aforementioned U.S. Pat. No. 5,951,604 "Scheker", with the only change being that some of the distal end of the radius probably will need to be excised in order to receive the articular socket 26. At this point, the radial brace member 12 is secured onto the radius 22, the ulnar brace member 16 is secured onto the ulna 24, and the ball 18 is secured within the spherical recess to form a ball joint.

Next, the proximal ends of the carpal bones are excised to fit flat against the distal plate 58 of the articular member 28. With the wrist bent downwardly, holes are drilled in the carpal bones as required (and preferably with the aid of a template) to receive the fasteners 70A, 70B. Then, the fasteners 70A, 70B are extended through the openings 68 in the distal plate 58 and into the holes that have been drilled in the carpal bones, and the fasteners 70A, 70B are rotated to thread them into the threaded openings 68 in the distal plate 58. The head end of the fasteners 70A, 70B has a recess (not shown) that allows a rotational driver such as a screwdriver or Allen wrench to rotationally drive the fasteners. The screw 70A also is threaded into the hole that has been drilled in its respective carpal bone, thereby securing the distal plate 58 to the carpal bones. The screw 70A prevents the distal plate 58 from pulling away from the carpal bones, and the pins 70B prevent the distal plate 58 from rotating or sliding relative to the carpal bones. While one screw 70A and two pegs 70B are shown, any combination of screws and pegs may be used, as well as other means for securing the distal plate 58 to the carpal bones of the wrist.

The wrist is then pushed back up, being careful to align the tear-shaped projections 66 in the distal plate 58 with the tear-shaped cavities 62 in the base 56, while the base 56 lies in the cavity 52 of the articular socket 26, until the tear-shaped projections 66 in the distal plate 58 snap into the tear-shaped cavities 62 in the articular surface member 56. The existing tendons and ligaments of the wrist retain the articular member 28 in the articular socket 26 at the distal radius. This arrangement allows a full range of motion, as well as providing support of the wrist joint by the radius 22 and the ulna 24. It also should be noted that the distal plate 58 and the corresponding ellipsoidal surfaces of the articular member 28 and the articular socket 26 extend across the full width of the wrist in order to provide a large supporting surface area. These surfaces extend from a point outside of (or beyond) the longitudinal axis of the radius 22 to a point outside of (or beyond) the central axis of the hemispherical recess that receives the ball 18 (i.e. the axis of the rod 16), thus extending for a width that is greater than the distance between the longitudinal axis of the radius 22 and the center of the hemispherical recess. As shown in FIG. 2, the ellipsoidal surfaces of the articular member 28 and the articular socket 26 extend in the radial direction beyond the radius abutment surface of the elongated portion 30 and extend in the ulnar direction beyond the center point of the hemispherical recess. In fact, in this embodiment, the concave ellipsoidal surface 52 of the articular socket 26 extends beyond the end of the base 20 (beyond the center of the hemispherical recess), projecting over a portion of the cover 40, and above the outer edge of the ball 18. Thus, the wrist portion of the prosthesis 10 is well-supported over a large surface area of surface-to-surface contact as the articular member 28 slides within the articular socket 26. It is also well-supported by both the radius 22 and the ulna 24 while permitting a full range of motion between the radius and ulna. This permits the wrist joint to support a substantial amount of weight or loading without causing pain and without damaging the joint, while providing a full range of motion.

Figure 4:
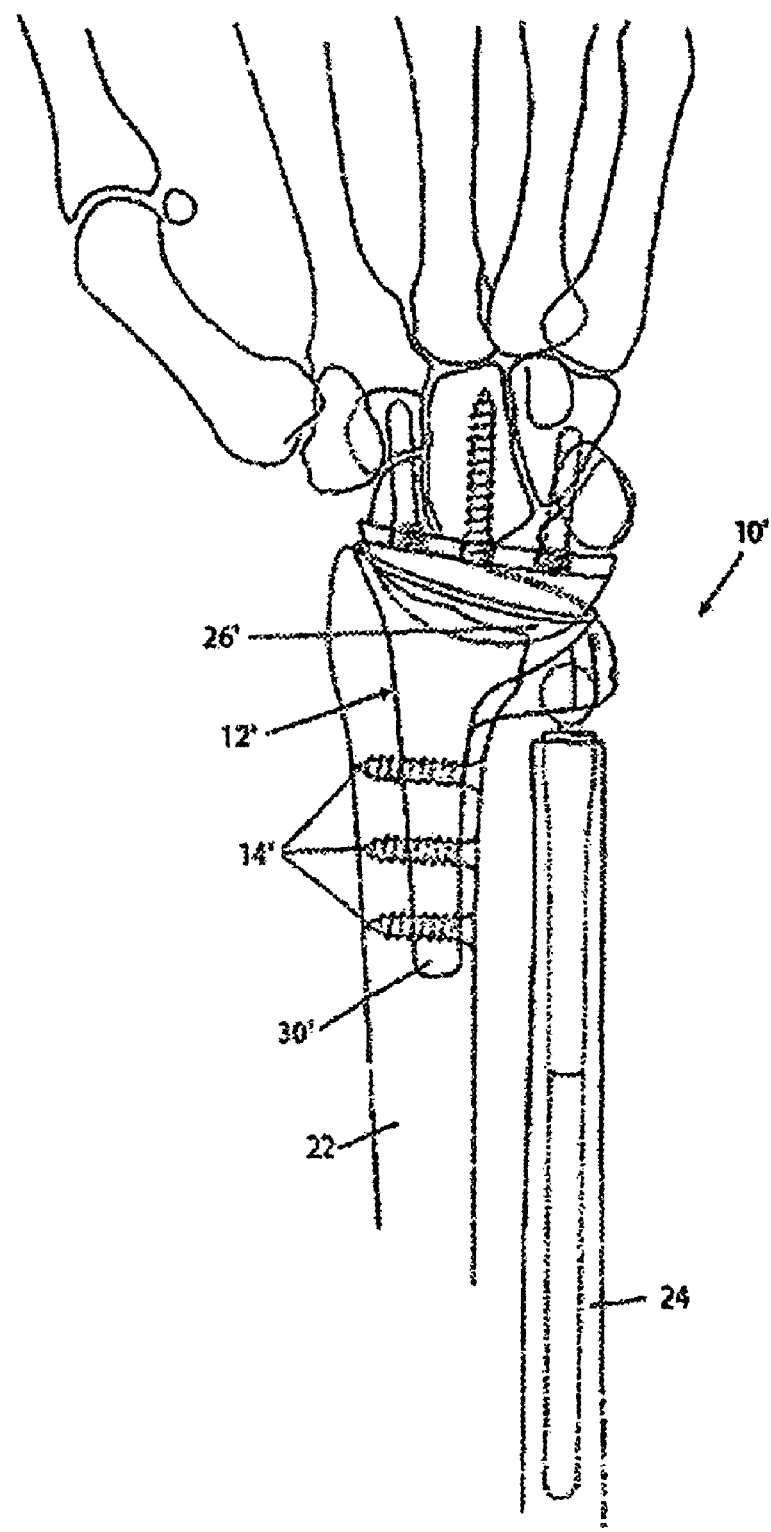
FIG. 4 is a view similar to FIG. 2, but for a second embodiment of an installed wrist and distal radioulnar joint prosthesis made in accordance with the present invention.
Figure 5:
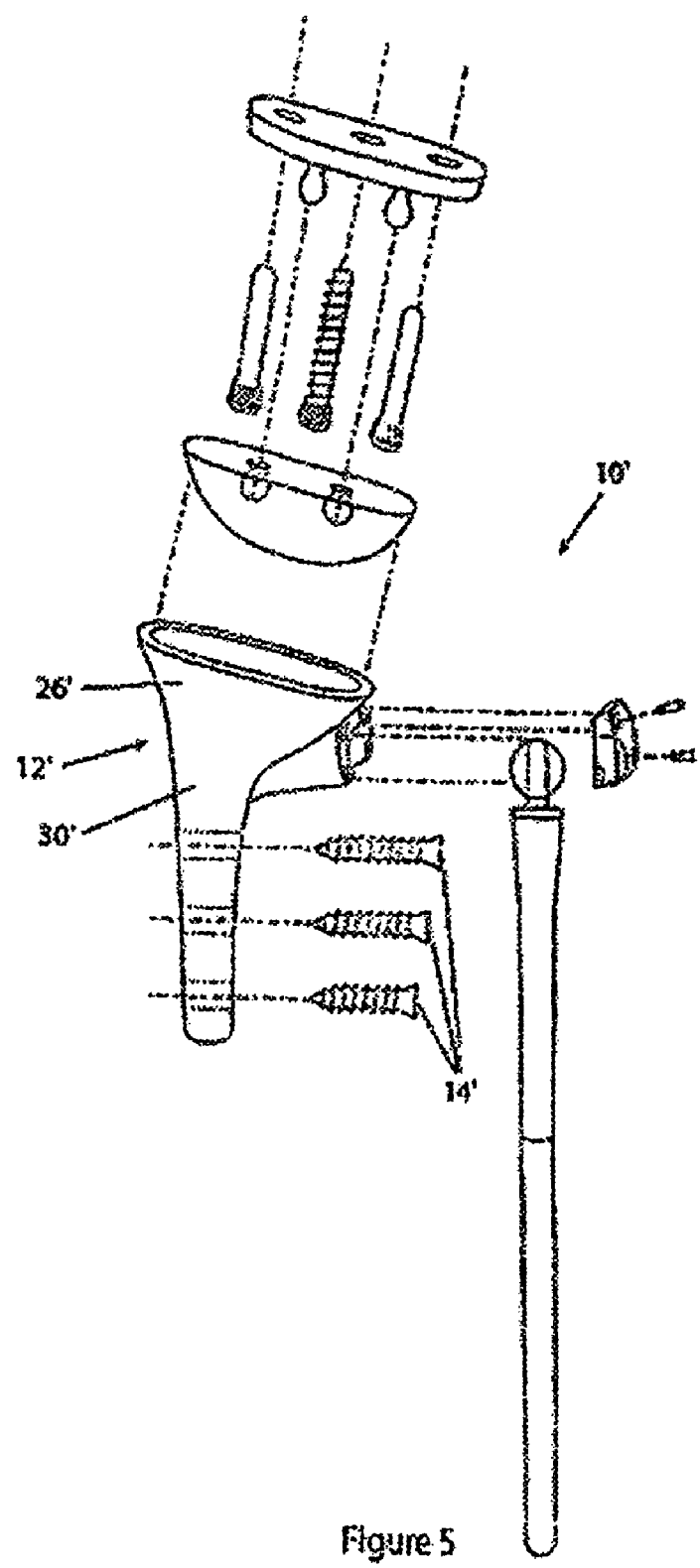
FIG. 5 is an exploded, perspective view of the wrist and distal radioulnar joint prosthesis of FIG. 4.

FIGS. 4 and 5 show a second embodiment of a total wrist and distal radioulnar joint replacement prosthesis 10' made in accordance with the present invention. This embodiment 10' is very similar to the first embodiment 10 described above, except that the location and installation of the radial brace member 12' is different. In this embodiment, the radial brace member 12' is inserted into the medullary cavity of the radius 22, and may make use of cement or other methods of attachment such as screws 14'. All the other components of this embodiment 10' and its method of operation remain substantially the same as in the first embodiment 10. This embodiment provides a larger contact surface area between the articular socket 26' and the elongated portion 30' of the radial brace member 12', which may result in greater structural integrity of the prosthesis 10'.

It will be obvious to those skilled in the art that modifications may be made to the embodiments described above without departing from the scope of the present invention.

What is claimed is:

1. A prosthesis for a total wrist and distal radioulnar joint replacement, comprising:
an ulnar brace member including a rod defining a longitudinal axis, and a ball slidably mounted to said rod for translation along said longitudinal axis relative to said rod;
a radial brace member defining a proximal end and a distal end, including a base at said distal end and a base cover releasably mounted to said base, wherein said base and said base cover define a substantially spherical cavity which receives and rotationally supports said ball; and wherein said radial brace further includes an articular socket at said distal end, said articular socket defining a concave ellipsoidal surface; and
an articular member defining a mating convex ellipsoidal surface which is slidably received in said concave ellipsoidal surface.

2. A prosthesis for a total wrist and distal radioulnar joint replacement as recited in claim 1, wherein said articular member includes a base member and a distal plate secured to said base member.

3. A prosthesis for a total wrist and distal radioulnar joint replacement as recited in claim 2, and further comprising means for securing said distal plate to the carpal bones.

4. A prosthesis for a total wrist and distal radioulnar joint replacement as recited in claim 3, wherein said securing means includes a screw.

5. A prosthesis for a total wrist and distal radioulnar joint replacement as recited in claim 4, wherein said screw has a head end which defines self-locking threads that are received in a threaded opening in said distal plate.

6. A prosthesis for a total wrist and distal radioulnar joint replacement as recited in claim 1, wherein said ulnar brace member includes means for mounting on the ulna bone of a patient, said radial brace member includes an elongated portion including means for mounting on the radius bone of the patient, and said articular member includes means for mounting on at least one carpal bone of the patient.

7. A prosthesis for a total wrist and distal radioulnar joint replacement as recited in claim 6, wherein the substantially spherical cavity of the radial brace member defines a center point, and said concave ellipsoidal surface extends substantially across the full width of the wrist, at least from a point outside of the elongated portion to a point beyond the center point of the spherical cavity.

8. A prosthesis for a total wrist and distal radioulnar joint replacement as recited in claim 6, wherein said articular member includes a base member and a distal plate secured to said base member, wherein said means for mounting the articular member on at least one carpal bone includes said distal plate.

9. A prosthesis for a total wrist and distal radioulnar joint replacement as recited in claim 8, wherein said means for mounting the articular member on at least one carpal bone includes an opening defined through said distal plate and a screw sized to extend through that opening.

10. A prosthesis for a total wrist and distal radioulnar joint replacement as recited in claim 9, wherein said opening is threaded and said screw has a threaded shaft and an enlarged head at the end of the threaded shaft, the enlarged head defining self-locking threads that are received in said threaded opening in said distal plate.

11. A prosthesis for a total wrist and distal radioulnar joint replacement as recited in claim 1, wherein said radial brace member includes an elongated portion including means for mounting to a radius bone; the substantially spherical cavity of the radial brace member defines a center point, and said concave ellipsoidal surface extends from a point outside of said elongated portion to a point beyond the center point of said spherical cavity.

12. A prosthesis for a total wrist and distal radioulnar joint replacement, comprising:

a radial brace member including an elongated portion having a radius abutment surface that conforms to the shape of the outer surface of a human radius, said elongated portion also defining a plurality of holes for receiving screws to secure the radial brace member to a radius;

said radial brace member having a proximal end and a distal end, including a base at said distal end and a base cover releasably mounted to said base, wherein said base and said base cover define a substantially spherical cavity which defines a center point; and wherein said radial brace further includes an articular socket at said distal end, said articular socket defining a concave ellipsoidal surface that extends from a point beyond the radius abutment surface in the radial direction to a point beyond the center point in the ulnar direction; and an articular member defining a mating convex ellipsoidal surface which is slidably received in said concave ellipsoidal surface and which also extends laterally from a point beyond the radius abutment surface in the radial direction to a point beyond the center point in the ulnar direction.

13. A prosthesis for a total wrist and distal radioulnar joint replacement as recited in claim 12, wherein said articular member includes means for mounting on at least one carpal bone.

14. A prosthesis for a total wrist and distal radioulnar joint replacement as recited in claim 13, and further comprising an ulnar brace member including a rod defining a longitudinal axis, and a ball slidably mounted to said rod for translation along said longitudinal axis relative to said rod, wherein said ball is received in said substantially spherical cavity.

15. A prosthesis for a total wrist and distal radioulnar joint replacement as recited in claim 14, wherein said radial member includes means for mounting said elongated portion on a human radius with said articular socket at the distal end of the radius.

* * * * *